United States Patent
Band et al.

(10) Patent No.: US 6,997,877 B2
(45) Date of Patent: Feb. 14, 2006

(54) METHOD FOR THE MEASUREMENT OF POST ARTERIOLAR PRESSURE

(75) Inventors: David Marston Band, Surrey (GB); Terence Kevin O'Brien, Cambridgeshire (GB); Christopher Bancroft Wolff, Cambridgeshire (GB)

(73) Assignee: Lidco Group PLC, London (GB)

( * ) Notice: Subject to any disclaimer, the term of this patent is extended or adjusted under 35 U.S.C. 154(b) by 20 days.

(21) Appl. No.: 10/486,926

(22) PCT Filed: Aug. 30, 2002

(86) PCT No.: PCT/GB02/03976

§ 371 (c)(1),
(2), (4) Date: Feb. 25, 2004

(87) PCT Pub. No.: WO03/020131

PCT Pub. Date: Mar. 13, 2003

(65) Prior Publication Data

US 2004/0254480 A1    Dec. 16, 2004

(30) Foreign Application Priority Data

Aug. 30, 2001   (GB) .................................. 0121054

(51) Int. Cl.
*A61B 5/00*   (2006.01)

(52) U.S. Cl. ...................... 600/485; 600/526; 600/505
(58) Field of Classification Search ................ 600/481, 600/490, 483–486, 492–496, 500–503, 508, 600/526

See application file for complete search history.

(56) References Cited

U.S. PATENT DOCUMENTS

| 4,807,638 A | 2/1989 | Sramek |
| 5,103,828 A | 4/1992 | Sramek |
| 6,071,244 A * | 6/2000 | Band et al. .................. 600/526 |
| 6,348,038 B1 * | 2/2002 | Band et al. .................. 600/485 |

FOREIGN PATENT DOCUMENTS

| WO | WO 9724982 A1 * | 7/1997 |
| WO | 98 02086 A | 1/1999 |
| WO | WO 9902086 A1 * | 1/1999 |

* cited by examiner

*Primary Examiner*—Robert L. Nasser
*Assistant Examiner*—Navin Natnithithadha
(74) *Attorney, Agent, or Firm*—Bacon & Thomas, PLLC

(57) ABSTRACT

A method for the measurement of post arteriolar pressure in a patient which is determined from information regarding the blood pressure (BP), systemic vascular resistance (R) and cardiac output (CO) by plotting the regression line for the equation BP=R×Q+c where c is the post arteriolar pressure, and determining the value of c from the regression line.

18 Claims, 1 Drawing Sheet

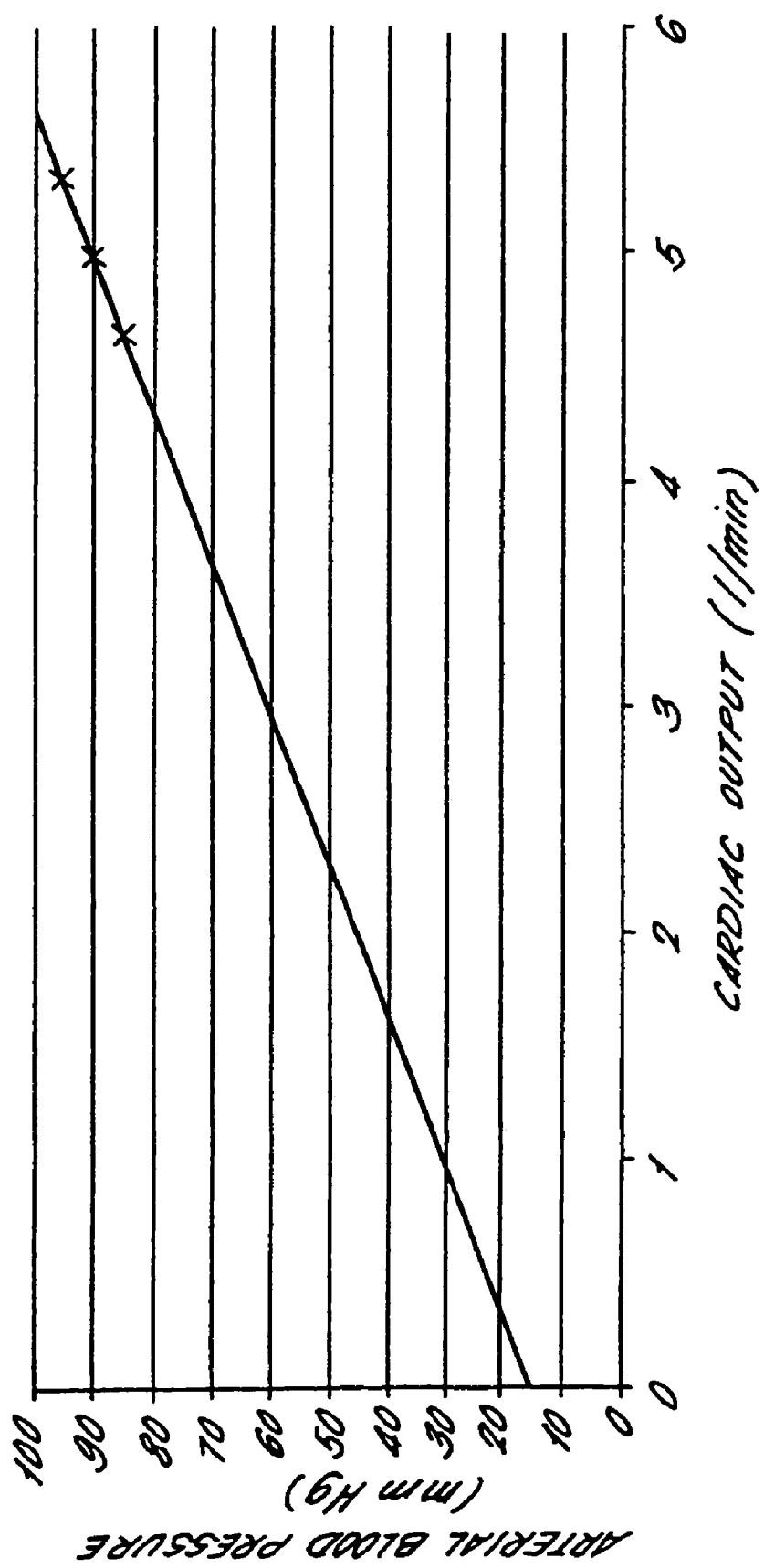

METHOD FOR THE MEASUREMENT OF POST ARTERIOLAR PRESSURE

The present invention relates to a method for the measurement of post arteriolar pressure in a patient.

By the term "post arteriolar pressure" as used herein is meant a theoretical pressure in the cardiovascular system. It is calculated from the relationship between short term variations in cardiac output (CO) and mean arterial pressure (MAP) occurring against a background of a constant systemic vascular resistance. Such variations may occur naturally or be induced. In a typical patient arterial pressure and cardiac output fluctuate with the respiratory cycle. We have discovered that if the beat to beat variations are plotted as an x y graph then they fall on a line that has an intercept on the pressure axis. This pressure we term the "post arteriolar pressure".

If the mean arterial pressure (MAP) is taken an 100 mm Hg then the pressure at the proximal end of the capillaries is typically 30 mm Hg and at the distal end is 12–15 mm Hg.

Apart from the MAP these pressures cannot be measured clinically and are only known from physiological experiments.

The pressure drop from 100 to 30 mm Hg occurs at the arterioles which are the terminal branches of the arterial system. These control the resistance flow. This resistance is known as the systemic vascular resistance (SVR). It may be calculated as $$SVR = MAP/CO.$$

Most clinicians subtract the right atrial pressure (RAP) from the MAP before dividing by the CO. The right atrium is at the end of the venous system and the correction for RAP is an attempt to use the pressure drop across the system rather than the absolute pressure for the calculation. It can be appreciated that the SVR is defined in terms of pressure and flow and cannot be measured directly. It is used extensively for regulating the use of vasoactive drugs.

Measurement of the post arteriolar pressure in a patient would be advantageous to a surgeon or physician since a high reading would indicate that the patient was retaining fluid in the right side of the heart/circulation, whilst a low reading would indicate that the patient required an infusion of fluid. Continuous monitoring of the post arteriolar pressure would thus provide an important diagnostic tool for the surgeon or physician.

Accordingly, the present invention provides a method for determining the post arteriolar pressure in a patient, which method comprises the steps of:—

(i) recording and storing the arterial blood pressure waveform of a patient from a blood pressure monitoring device over a period of time;

(ii) determining the nominal or actual stroke volume associated with each arterial blood pressure waveform;

(iii) obtaining the nominal or actual cardiac output from the data in step (ii); and (iv) plotting the regression line for the equation $$BP = R \times Q + c$$

where

BP is the blood pressure,

R is the systemic vascular resistance,

Q is the cardiac output, and c is the post arteriolar pressure, and (v) determining the value of the post arteriolar pressure from the regression line.

In carrying out the method of the present invention the patient's arterial blood pressure in step (i) may be monitored continuously by conventional means from, for example, the aorta, the brachial artery, femoral artery or the radial artery. Accordingly, the patient's arterial blood pressure may be monitored using an arterial catheter with a transducer system or a non-invasive method. The output from the pressure measuring device preferably provides the blood pressure over at least one respiratory cycle. The blood pressure is preferably analysed on a beat-to-beat basis over a period of at least 4 seconds, preferably over a period of at least 10 seconds and more preferably is continuously monitored.

The nominal stroke volume in step (ii) of the method is generally determined via a cardiac output measuring method, such as a pressure waveform analysis, a Doppler method, measuring impedance changes or an indicator dilution method. The preferred method for use in the present invention is a pressure waveform method, for example a method as described in WO97/24982 in which a non-linear transformation is used to correct for the changing characteristics of the arterial system with pressure and autocorrelation is then used to derive the cardiac output, or a method as described in WO99/02086 in which the data obtained in step (i) is subjected to a Fourier analysis in order to obtain the modulus of the first harmonic and the nominal stroke volume is obtained from the modulus of the first harmonic and data relating to the arterial blood pressure and the heart rate. Using this technique the cardiac output of each beat of the heart is calculated and displayed.

When using the method as described in WO99/02086 the nominal stroke volume is obtained from the following equation $$\text{nominal stroke volume} = \frac{\text{modulus of first harmonic of blood pressure waveform}}{e^{+0.0092 \times MAP} \times HR}$$

where e is the base of natural logarithms

MAP is the mean arterial blood pressure, and

HR is the heart rate.

The nominal cardiac output may be obtained using the nominal stroke volume and heart rate. The nominal cardiac output may found, for example, by multiplying the nominal stroke volume by the heart rate. If more than one beat is used to calculate the nominal cardiac output then it may be calculated as the sum of the stroke volumes divided by the sum of the durations of each beat. It will be understood that the nominal stroke volume and the nominal cardiac output are uncalibrated and may be converted into the calibrated data, if desired. This is performed by multiplying the nominal stroke volume by a calibration factor to give the true stroke volume, as found by another method. The cardiac output may then be calculated from the true stroke volume and heart rate.

The regression line for the equation given in step (iv) is obtained by plotting the blood pressure against the cardiac output, for example by means of a computer. If the blood pressure is plotted on the y-axis and the cardiac output plotted on the x-axis the point where the regression line crosses the y-axis is the value of the post arteriolar pressure. The value of the post arteriolar pressure may be displayed on a computer screen and optionally may be continuously updated.

The x y plot described above can be interpreted in two ways. The slope of the line is a new estimation of the peripheral resistance. The intercept on the pressure axis is the notional pressure beyond the resistance. The major clinical importance of the discovery is that it provides an estimate of the back pressure on the circulation. This is related to the degree of fluid loading and venous tone of the circulation.

It is clear that any natural or induced changes in cardiac output/mean arterial pressure that occur against an unchanging SVR will allow the calculation of the post arteriolar pressure. For example, a clinician could pace the patient's heart at 100 beats per minute and then at 80 beat per minute. The mean arterial pressure versus mean cardiac output at both heart rate levels is then plotted and from the regression line the post arteriolar pressure is obtained.

Apparatus for carrying out the present invention may comprise any suitably programmed computer such as an IBM compatible computer or a Macintosh computer which is able to acquire data from the blood pressure measurement device or monitor. It may also be integrated with software and hardware for preforming other tasks. For example, the device may be capable of carrying out the present invention as well as the method used for calibration or other monitoring tasks. The computer programme running on the computer may then either display the results on a visual display unit or can output this information to some other device.

The present invention will be further described, by way of example, with reference to the accompanying drawings in which:

FIG. 1 is a graph of the arterial blood pressure against cardiac output for a patient measured over one respiratory cycle.

The following data could be obtained from a patient over a respiratory cycle

|  | Blood Pressure (BP) | Cardiac Output (Q) |
| --- | --- | --- |
| Top of Oscillation | 95 | 5.33 |
| Bottom of Oscillation | 85 | 4.67 |
| Mean | 90 | 5.00 |

These results may be plotted as a regression line as shown in FIG. 1. The point where the regression line crosses the x-axis in FIG. 1 at 15 mm Hg is the post arteriolar pressure of the patient at that time.

It is considered that a post arteriolar pressure of about 15 mm Hg would be normal for a healthy patient. However, a post arterial pressure reading of say 30 mm Hg would indicate that the patient was filling up with fluid and developing oedema, whilst a reading of say 10 mm Hg would indicate that the patient was low on fluids and required fluid replenishment.

What is claimed is:

1. A method for determining the post arteriolar pressure in a patient, which method comprises the steps of:
   (i) recording and storing the arterial blood pressure waveform of a patient from a blood pressure monitoring device over a period of time;
   (ii) determining the nominal or actual stroke volume associated with each arterial blood pressure waveform;
   (iii) obtaining the nominal or actual cardiac output from the data in step (ii); and
   (iv) plotting the regression line for the equation $$BP = R \times Q + c$$

where
   BP is the blood pressure,
   R is the systemic vascular resistance,
   Q is the cardiac output, and
   c is the post arteriolar pressure, and
   (v) determining the value of the post arteriolar pressure from the regression line.

2. A method as claimed in claim 1 wherein the arterial blood pressure is plotted in step (i) for a period of up to ten seconds.

3. A method as claimed in claim 1 wherein the arterial blood pressure is analysed on a beat-to-beat basis.

4. A method as claimed in claim 1 wherein the stroke volume in step (ii) is determined via a cardiac output measuring method.

5. A method as claimed in claim 4 wherein the cardiac output measuring method is a pressure waveform analysis.

6. A method as claimed in claim 5 wherein the data obtained in step (i) is subjected to Fourier analysis in order to obtain the modulus of the first harmonic and the nominal stroke volume is obtained from the modulus of the first harmonic and data relating to the arterial blood pressure and the heart rate.

7. A method as claimed in claim 6 wherein the nominal stroke volume is obtained from the following equation $$\text{nominal stroke volume} = \frac{\text{modulus of first harmonic of blood pressure waveform}}{e^{+0.0092 \times MAP} \times HR}$$

where
e is the base of natural logarithms
MAP is the mean arterial blood pressure, and
HR is the heart rate.

8. A method as claimed in claim 1 wherein the regression line in step (iv) is plotted by means of a computer.

9. A method as claimed in claim 8 wherein the value of the post arteriolar pressure is displayed on a computer screen and optionally continuously updated.

10. A method as claimed in claim 2 wherein the arterial blood pressure is analysed on a beat-to-beat basis.

11. A method as claimed in claim 2 wherein the stroke volume in step (ii) is determined via a cardiac output measuring method.

12. A method as claimed in claim 3 wherein the stroke volume in step (ii) is determined via a cardiac output measuring method.

13. A method as claimed in claim 2 wherein the regression line in step (iv) is plotted by means of a computer.

14. A method as claimed in claim 3 wherein the regression line in step (iv) is plotted by means of a computer.

15. A method as claimed in claim 4 wherein the regression line in step (iv) is plotted by means of a computer.

16. A method as claimed in claim 5 wherein the regression line in step (iv) is plotted by means of a computer.

17. A method as claimed in claim 6 wherein the regression line in step (iv) is plotted by means of a computer.

18. A method as claimed in claim 7 wherein the regression line in step (iv) is plotted by means of a computer.

* * * * *